United States Patent
Mizrach et al.

(10) Patent No.: US 11,690,358 B2
(45) Date of Patent: Jul. 4, 2023

(54) SYSTEMS AND METHODS FOR CHICKS SEXING AND HEALTH ASSESSMENT OF NEWLY-HATCHED CHICKS

(71) Applicants: The State of Israel, Ministry of Agriculture & Rural Development, Agriculture Research Organization, Rishon Lezion (IL); ESHET EILON INDUSTRIES LTD., Kibbutz Eilon (IL)

(72) Inventors: Amos Mizrach, Rishon Lezion (IL); Victor Alchanatis, Raanana (IL); Nachshon Shamir, Moshav Kidron (IL); Lavi Rosenfeld, Rishon Lezion (IL); Clara Shenderey, Nesher (IL); Asher Levi, Ashdod (IL); Viacheslav Ostrovsky, Rishon Lezion (IL); Menashe Tamir, Moshav Yodfat (IL); Reuven Shadmi, Kibbutz Elion (IL); Avishay Tamir, Moshav Yodfat (IL)

(73) Assignees: The State of Israel, Ministry of Agriculture & Rural Development, Agriculture Research Organization, Rishon Lezion (IL); ESHET EILON INDUSTRIES LTD., Kibbutz Eilon (IL)

( * ) Notice: Subject to any disclaimer, the term of this patent is extended or adjusted under 35 U.S.C. 154(b) by 0 days.

(21) Appl. No.: 17/429,952

(22) PCT Filed: Dec. 6, 2020

(86) PCT No.: PCT/IB2020/061567
§ 371 (c)(1),
(2) Date: Aug. 11, 2021

(87) PCT Pub. No.: WO2021/111420
PCT Pub. Date: Jun. 10, 2021

(65) Prior Publication Data
US 2022/0132811 A1      May 5, 2022

Related U.S. Application Data

(60) Provisional application No. 62/943,881, filed on Dec. 5, 2019.

(51) Int. Cl.
*A01K 45/00* (2006.01)
*G06V 40/10* (2022.01)

(52) U.S. Cl.
CPC .............. *A01K 45/00* (2013.01); *G06V 40/10* (2022.01); *G06V 2201/03* (2022.01)

(58) Field of Classification Search
CPC ..... A01K 45/00; G06V 40/10; G06V 2201/03
(Continued)

(56) References Cited

U.S. PATENT DOCUMENTS 3,742,232 A * 6/1973 Koehn ................... A24C 5/321
701/99
6,396,938 B1 * 5/2002 Tao ........................ A01K 45/00
382/110
(Continued)

FOREIGN PATENT DOCUMENTS

| CN | 102169539 | * 8/2012 | ............... G06K 9/00 |
| CN | 211070913 U | 7/2020 | |

(Continued)

OTHER PUBLICATIONS

Yakov Gershman, "A simple way to determine the sex of one-day poultry chickens".
Jones, P. T. et al., "Edge Extraction Algorithm for Feather Sexing Poultry Chicks", 1991, American Society of Agricultural Engineers, vol. 34(2), pp. 635-640.

*Primary Examiner* — Jin Ge
(74) *Attorney, Agent, or Firm* — Mark M. Friedman (57) ABSTRACT

The present invention provides a system and method for recognizing and segregating chicks by sex according to their feathers pattern. The system and method are based on the instinctive reaction of chicks to spread their wings in order to maintain stability in response to instantaneous disorientation, for example, due to a sudden change in spatial movement. The present invention further features a weighing system and a system for detecting external body defects of chicks for assessing chicks' health.

25 Claims, 6 Drawing Sheets

(58) Field of Classification Search
USPC .......................................................... 119/713
See application file for complete search history.

(56) References Cited

U.S. PATENT DOCUMENTS

| | | |
|---|---|---|
| 8,019,125 B2 | 9/2011 | Nadreau et al. |
| 10,806,124 B2 | 10/2020 | Karimpour |
| 2001/0030146 A1* | 10/2001 | Yavnai ................... A01K 45/00 |
| | | 206/315.9 |
| 2001/0035370 A1 | 11/2001 | Yavnai et al. |
| 2009/0000915 A1* | 1/2009 | Nadreau ................... B07C 5/34 |
| | | 198/469.1 |
| 2018/0343830 A1* | 12/2018 | Karimpour .......... A61B 5/7282 |
| 2018/0353081 A1* | 12/2018 | Karimpour .............. A61D 7/00 |

FOREIGN PATENT DOCUMENTS

| | | | |
|---|---|---|---|
| EP | 2579188 B1 | 3/2018 | |
| JP | H06245662 | * 9/1994 | ............. A01K 45/00 |

* cited by examiner

SYSTEMS AND METHODS FOR CHICKS SEXING AND HEALTH ASSESSMENT OF NEWLY-HATCHED CHICKS

CROSS-REFERENCES TO RELATED APPLICATIONS

This application is related to and claims priority from commonly owned U.S. Provisional Patent Application Ser. No. 62/943,881, entitled: A System for Feather Sexing of Chicks, filed on 5 Dec. 2019, the disclosure of which is incorporated by reference in its entirety herein.

TECHNICAL FIELD

The present invention relates to the field of identifying and assessing newly-hatched chick's gender and health.

BACKGROUND OF THE INVENTION

Chick sexing is the method of distinguishing the gender of chickens and other hatchlings, usually by a trained person called a chick sexer or chicken sexer. Chick sexing is practiced mostly by large commercial hatcheries to separate female chicks or "pullets" (destined to lay eggs for commercial sale) from the males or "cockerels" (most of which are killed within days of hatching because they are irrelevant to egg production).

Identification of the gender of newly-hatched chicks can be achieved for most species of chicks by feather sexing. Feather sexing is the ability to detect the gender of a newly-hatched chick based on the rate of growth of its wing feathers, which differ with gender due to genetic encoding. In an outstretched position, the female wings display a pattern of long feathers in the primary row and short feathers in the secondary row, while the male wings display a pattern of feathers of the same length in the primary and secondary rows.

Assessment of newly-hatched chicks' health is achieved for the most part by observing the chicks and identifying signs related to healthy chicks such as bright-eyed, alert and active, head configuration, beak configuration, legs configuration, and the like.

To date, health assessment and gender recognition of newly hatched poultry chicks are performed manually, involving the need to observe each chick with a naked eye, and spread its wings so as to determine its health and gender, respectively.

SUMMARY OF THE INVENTION

The present invention provides systems and methods for recognizing and segregating chicks by gender. The system is based on the instinctive reaction of chicks to spread their wings in order to maintain stability in response to instantaneous disorientation caused by an external factor, for example, due to a sudden change in spatial movement.

The present invention further features a weighing system and a system for detecting external body defects of chicks for assessing chicks' health.

Embodiments of the invention are directed to a system for recognizing and segregating chicks by gender according to their feathers pattern comprising: a separation unit including at least one conveyor extending at least partially through the separation unit, the at least one conveyor configured to maintain a forward moving path of the plurality of chicks in a queue; a sorting unit configured to receive the plurality of chicks in a queue, the sorting unit includes: at least one conveyor extending at least partially through the sorting unit configured to maintain a forward moving path; and, at least one container in communication with the at least one conveyor such that the at least one container is moved between a first position and a second position, while containing at least one chick of the plurality of chicks; and, an optic unit including a camera configured to capture at least one image of the at least one chick as the at least one container is moved between the first position and the second position, the at least one image is then transferred to be image processed so as to determine the gender of the at least one chick.

Optionally, the at least one container is in communication with the at least one conveyor through a moving element.

Optionally, the movement of the at least one container between the first position and the second position is achieved through the movement of a pin portion of the moving element along a slanting section.

Optionally, concurrently with the movement of the at least one container between the first position and the second position an intermediate portion of the moving element is vertically moveable along the at least one conveyor.

Optionally, the moving element is controlled by the computerized controller.

Optionally, the moving element includes a turning aside mechanism designed to allow the removal of the container's content.

Optionally, the turning aside mechanism is controlled by the computerized controller.

Optionally, the system additionally comprising a computerized controller configured for controlling the at least one conveyor and the camera.

Optionally, the at least one conveyor is one of: a belt conveyor, a U-shaped belt conveyor, a chain conveyor, a live roller conveyor, and a combination thereof.

Optionally, the at least one container has the shape of an inverted pyramid with a flattened vertex.

Optionally, the camera is a high-speed Charge Coupled Device (CCD) camera.

Optionally, the optic unit further includes a light source.

Optionally, the light source is a LED light source.

Optionally, the light source is controlled by the computerized controller.

Optionally, the system additionally comprising a segregating unit including at least one gate configured to receive the at least one chick from the at least one container.

Optionally, the segregating unit is controlled by the computerized controller.

Optionally, the system additionally comprising a counting machine configured to monitor the number of chicks passing through the at least one gate.

Optionally, the counting machine is controlled by the computerized controller.

Optionally, the system additionally comprising a packaging machine configured to receive chicks from the at least one gate and pack them in a crates suitable for transporting chicks.

Optionally, the packaging machine is controlled by the computerized controller.

Optionally, the one or more images are additionally used to detect body defects in the at least one chick.

Optionally, the system additionally comprising a weighing unit connected to the at least one conveyor of the sorting unit, the weighing unit includes a load cell configured to perform a plurality of weight readings of the at least one chick as the container reaches it so as to determine the health of the at least one chick based on its weight.

Optionally, the weighing unit is in controlled by the computerized controller.

Optionally, the load cell is in communication with a processor configured to calculate the actual weight of the at least one chick.

Embodiments of the invention are directed to a method for recognizing and segregating chicks by gender according to their feathers pattern comprising: placing the chicks along a first pathway for causing movement of the plurality of chicks in a queue; placing each of the plurality of chicks in a queue in a container, the container is placed along a second pathway so as to cause movement of the container between a first position and a second position, which causes the each of the plurality of chicks to spread its wings; capturing one or more images of the wings of the each of the plurality of chicks as the container is moved between the first position and the second position; and, processing the one or more images of the wings of the at least one chick so as to determine its gender.

Optionally, the movement of the container between the first position and the second position includes a passage along a slanting section.

Optionally, the method additionally comprising sorting the chicks according to their gender.

Optionally, the method additionally comprising counting the chicks of each gender.

Optionally, the one or more images of the chick is further used to identify body defects.

Optionally, the body defects are one of: plume problems, defective head, rotated head, crossed beak, and a combination thereof.

Optionally, the method additionally comprising: performing a plurality of weighing readings to each of the plurality of chicks as the container reaches a designated location within the second pathway; and, calculating the average of the plurality of weighing readings so as to determine the weight of each of the plurality of chicks and by that determine its health.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings.

DETAILED DESCRIPTION OF THE INVENTION

The present invention is not limited in its application to the details of construction and the arrangement of the components set forth in the following description. The invention is capable of other embodiments, or of being practiced or carried out in various ways. Also, it is to be understood that the phraseology and terminology employed herein is for the purpose of description and should not be regarded as limiting.

The present invention provides systems and methods for recognizing and segregating chicks by gender based on their wing pattern. The present invention relies on chicks' instinctive reaction to spread their wings to maintain stability in response to instantaneous disorientation.

Figure 1:
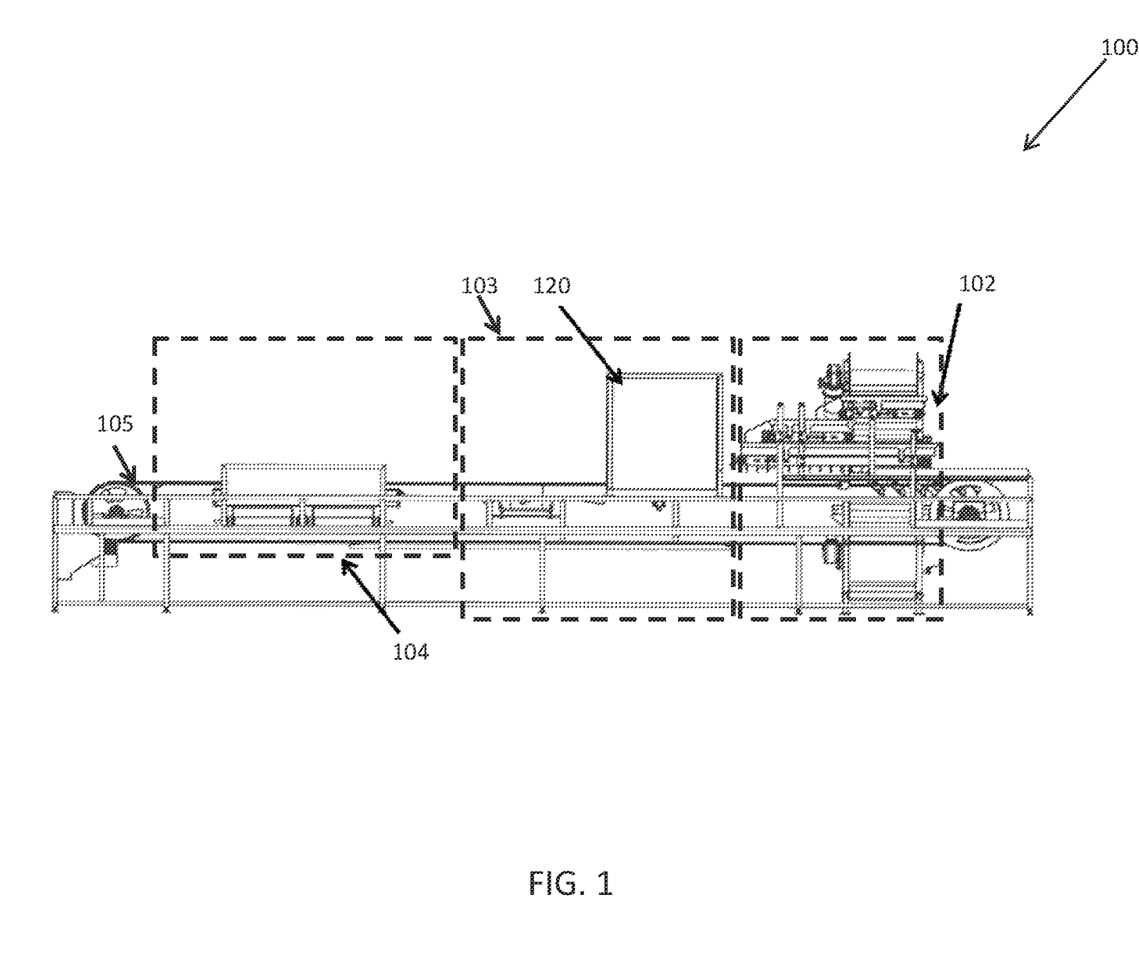
FIG. 1 is a perspective view of the system for recognizing and segregating chicks by gender according to an embodiment of the present invention.

FIG. 1 is a perspective view of system 100. The system 100 includes a separation unit 102 having one or more conveyors, a sorting unit 103, and a segregating unit 104. The system 100 further includes a conveyor 105, which is, for example, a belt conveyor extending at least partially through the separation unit 102, the sorting unit 103, and the segregating unit 104.

Figure 2:
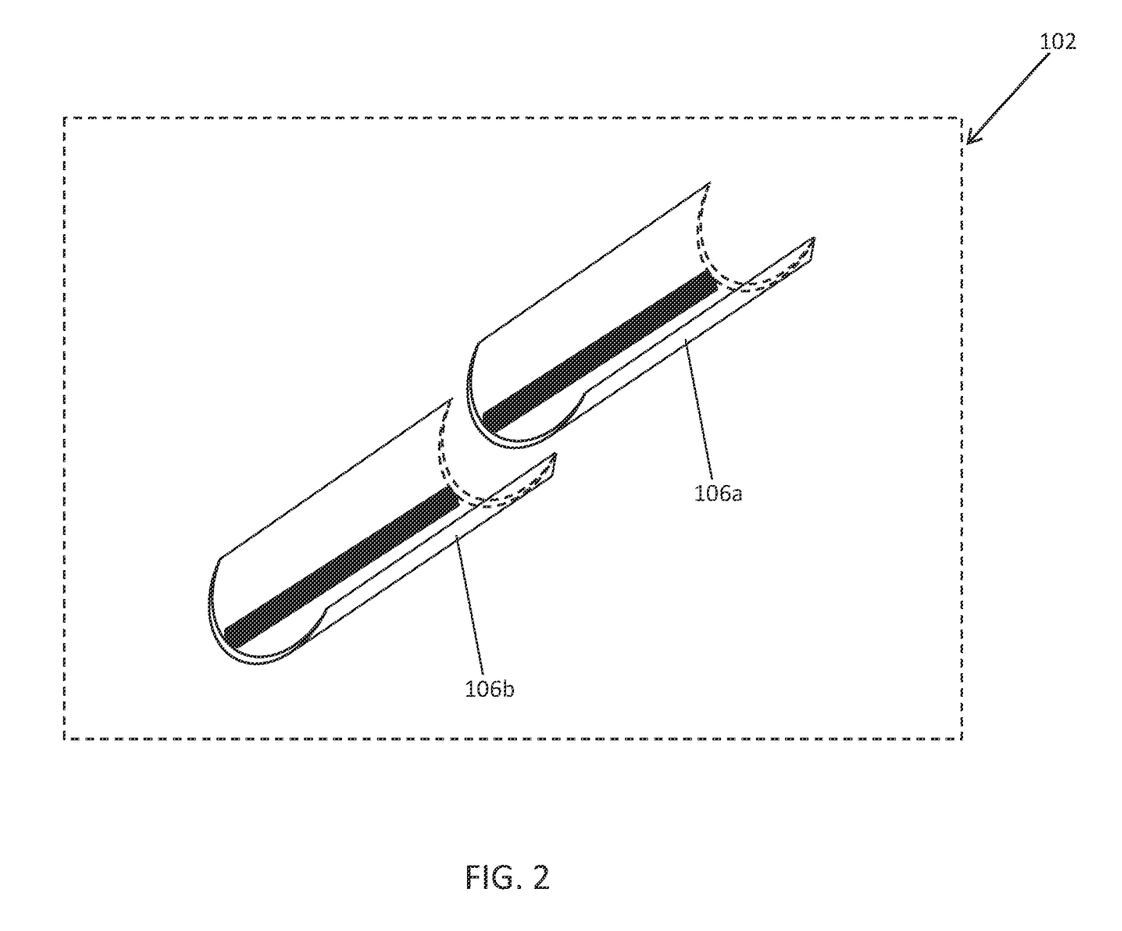
FIG. 2 is a perspective view of the separation unit of the system of FIG. 1.

The separation unit 102, best seen in FIG. 2, includes, for example, a first conveyor 106a and a second conveyor 106b extending at least partially through the separation unit 102 and configured to receive a plurality of chicks (not shown). The first and second conveyors 106a-106b, which are, for example, belt conveyors, are positioned sequentially one after the other and are in communication with one another so as to maintain a forward moving path.

The conveyors, which are either portions of the conveyor 105 or separate conveyors, may operate at the same or different speeds, and may be activated manually or controlled by a computerized controller (not shown), over wired and/or wireless networks, or combinations thereof.

The separation unit 102 may be in communication with other conveyors placed before it. These conveyors provide chicks into the separation unit 102 and may be, for example, a belt conveyor, a U-shaped conveyor, a chain conveyor, a live roller conveyor, and the like.

Figure 3:
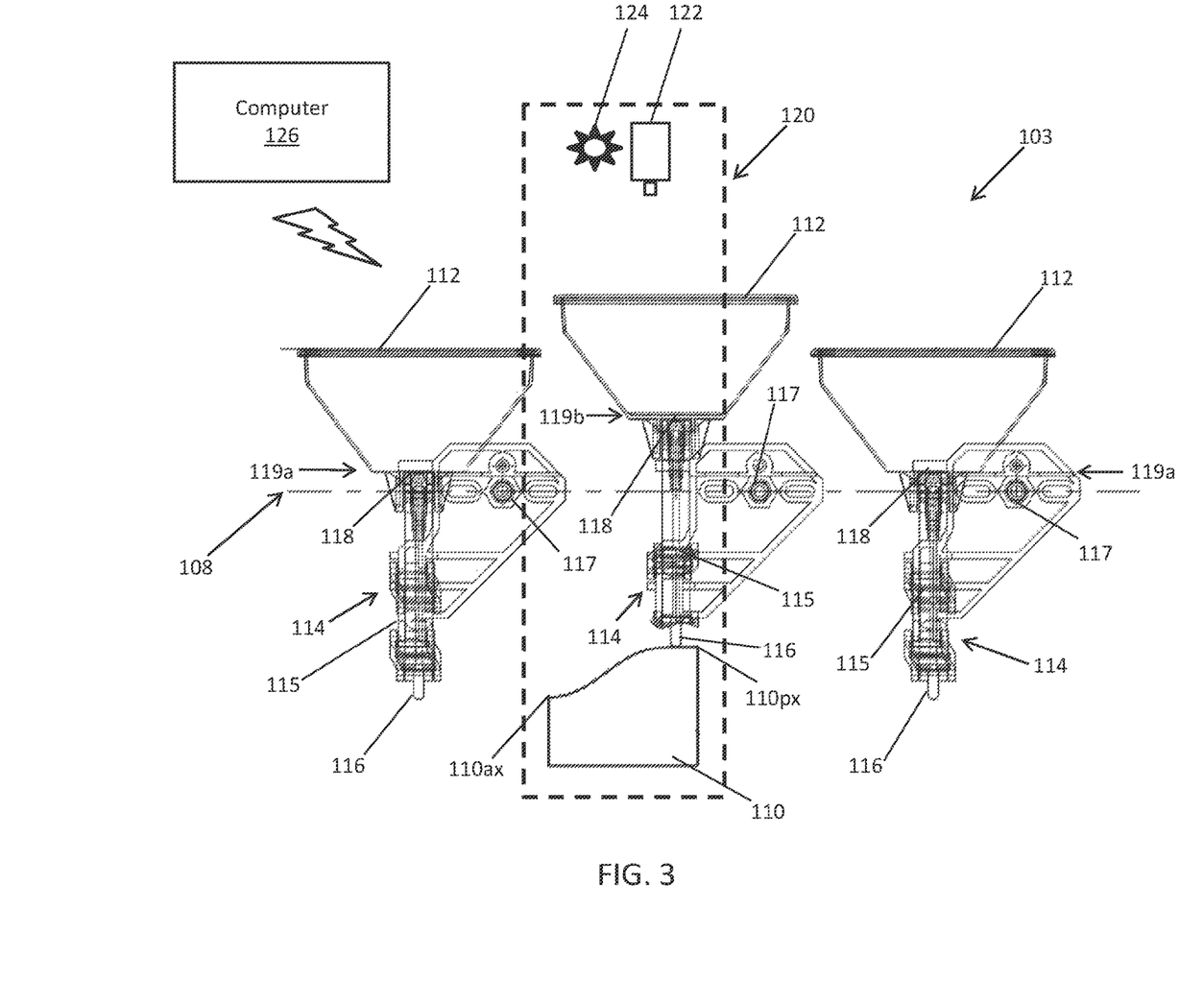
FIG. 3 is a perspective view of the sorting unit of the system of FIG. 1, which forces the instability of chicks causing them to wide spread their wings.

The sorting unit 103, best seen in FIG. 3, includes a slanting section 110 extending from a proximal portion 110ax to a distal portion 110px, and a conveyor 108, which is, for example, a belt conveyor. The conveyor 108, which is either a portion of the conveyor 105 or a separate conveyor, extends at least partially through the sorting unit 103 and may be controlled by a computer, computerized controller, or the like, as well as manually.

The sorting unit 103 further includes one or more containers, for example, a container 112 configured to receive a single chick. The container 112, which may be of different shapes, for example, an inverted pyramid with a flattened vertex, is in communication with the conveyor 108 and the slanting section 110 through, for example, moving element 114.

The moving element 114 includes, for example, a pin portion 116 configured to slide along the slanting section 110, a container portion 118 configured to connect between the moving element 114 and the container 112, an intermediate portion 115 configured to connect between the pin portion 116 and the container portion 118, and a conveyor portion 117 configured to connect the moving element 114 to the conveyor 108. The intermediate portion 115 is able to move vertically on the conveyor 108, in response to movement along the slanting section 110, so as to allow movement of the container 112 between a first position 119a, in which the container 112 is adjacent to the conveyor 108 (for example, at and before the proximal portion 110ax, as well as after the distal portion 110px), and a second position 119b, in which the container 112 is at a predetermined distance from the conveyor 108 (for example, at the distal portion 110px).

The moving element 114 may further incorporate a container content removal mechanism, for example, a turning aside mechanism. The turning aside mechanism, which may be controlled by a computer, computerized controller, or the like, as well as manually, is operated using, for example, an extension (not shown) that collides with either side of the bottom of the container 112, causing it to flip and release its content.

The sorting unit 103 further features an optic unit 120 covering at least a portion of the area of the slanting section 110. The optic unit 120 includes a camera 122, which is, for example, a high-speed Charge Coupled Device (CCD) camera or other camera suitable to achieve the same purpose, and a light source 124, which is, for example, a Light Emitting Diodes (LED) light source or other light source suitable to achieve the same purpose. The camera 122 and the light source 124 are positioned, for example, at the top of the optic unit 120, above the slanting section 110, and are in communication with a linked computer 126. "Linked" as used herein, includes both wired and/or wireless links, such that the computers, servers, components, devices and the like, are in electronic and/or data communications with each other, directly or indirectly.

The linked computer 126 is in further communication with the segregating unit 104. The segregating unit 104, positioned, for example, after the distal portion 110px, includes one or more gates, for example, three electromagnetic gates (not shown). Each electromagnetic gate represents, for example, a specific gender (male, female, or unrecognized gender) and is operated in response to a signal sent from the linked computer 126.

The gates may be in further communication with a counter or counting machine so as to monitor the number of chicks passing through each gate. The gates may also be in communication with a packaging machine including crates suitable for transporting chicks. Each crate receives a predetermined number of chicks, for example, 100 chicks per crate so as to be supplied to a customer.

In operation, chicks are entered into the separation unit 102 and are placed, either manually or automatically, on the first conveyor 106a. The chicks are moved, for example, in a horizontal movement from the first conveyor 106a towards the sorting unit 103, through the second conveyor 106b. The second conveyor 106b is operated, for example, at a speed, which is, for example, 10 percent faster than the speed of the first conveyor 106a. The difference in speeds enables creating a queue-like arrangement of chicks so as to feed the chicks to the sorting unit 103 one by one. The distance between every two chicks in the queue-like arrangement may be predetermined or random.

Figure 4A:
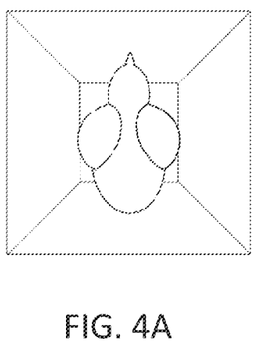
FIGS. 4A-E are top views illustrate the transition of the wings of a female chick from a folded position to an outstretched position and vice versa.
Figure 4B:
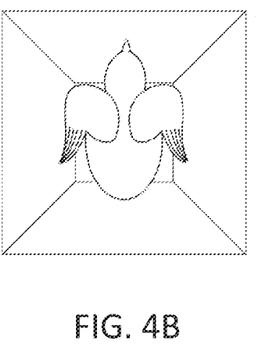
Figure 4C:
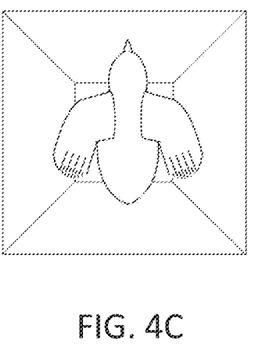
Figure 4D:
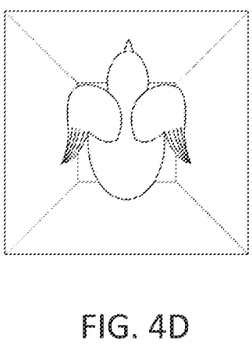
Figure 5A:
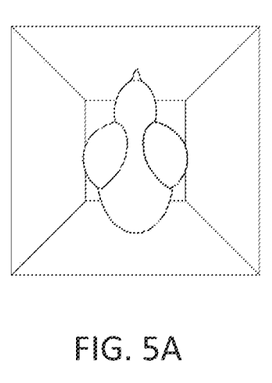
FIGS. 5A-E are top views illustrate the transition of the wings of a male chick from a folded position to an outstretched position and vice versa.
Figure 5B:
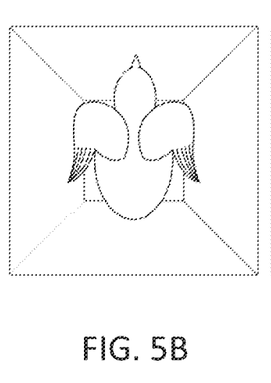
Figure 5C:
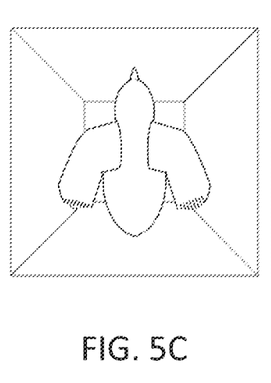
Figure 5D:
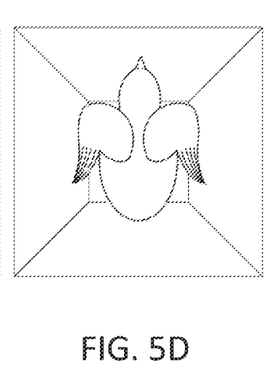
Figure 5E:
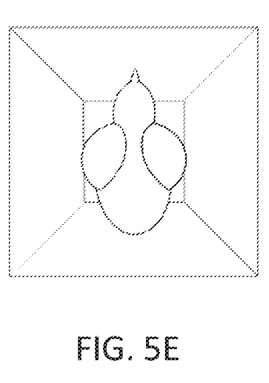

In the sorting unit 103, each chick is placed, either manually or automatically, in a separate container 112, positioned in its first position 119a. The containers are then moved sequentially one after the other by the conveyor 108, at a constant speed, towards the proximal portion 110ax of slanting section 110. The speed is, for example, identical to the speed of the second conveyor 106b allowing the chicks to relax and stay calm (FIGS. 4A and 5A).

Once the containers reach the proximal portion 110ax, the pin portion 116 of each moving element 114 moves along the route of the slanting section 110, from the proximal portion 110ax to the distal portion 110px. This movement causes the intermediate portion 115 of each moving element 114 to move vertically in relation to the conveyor 108, causing the containers to move from their first position 119a to their second position 119b. This movement, which causes a swift change in the container's height in relation to the conveyor 108, triggers an instinctive reaction of the chicks within the containers, causing them to spread their wings to maintain their stability in response to the instantaneous disorientation.

Simultaneously with each moving element's movement along the route of slanting section 110, the camera 122 obtains images of each chick within each container spreading its wings (FIGS. 4B-4D and 5B-5D). These images are then transferred to the linked computer 126, which determines the gender of the chick via image processing. The image processing occurs, for example, in real-time and includes: separating the chick pixels from the background, analyzing the chick's contour to select images of the chick with wings outstretched, extracting features relating to the chick's wings, and determining the chick's gender according to these features.

Figure 4E:
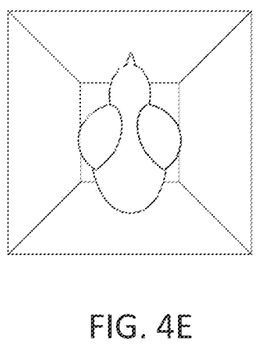

After the distal portion 110px, the intermediate portion 115 of each moving element 114 moves back to its initial position, causing each container to move back to its first position 119a. The conveyor 108 keeps a forward movement of each container 112 with its conveyor portion 117 towards the segregating unit 104 in a horizontal movement. This horizontal movement allows the chick within each container 112 to relax, regain balance, fold its wings, and return to an upright stance (FIGS. 4E and 4E).

With each container 112 reaching the segregating unit 104, a signal is sent from the linked computer 126 to the segregating unit 104. The signal leads to the opening of the designated electromagnetic gate (male, female, or unrecognized gender), according to the determination of gender performed by the image processing.

Once the container 112 reaches its designated gate, the chick is removed from the container 112 and transferred through the proper gender gate either manually or through the turning aside mechanism of the moving element 114.

In another embodiment of the present invention, the slanting section 110 is placed in reverse such that the movement of the container is in a reverse motion to the motion described above, from the distal portion 110px to the proximal portion 110ax. This movement also causes the chicks' instantaneous disorientation, which causes the chicks' instinctive reaction to spread their wings to maintain their stability.

The present invention further provides a weighing system and a system for detecting external body defects of chicks for assessing chicks' health. These systems can be independent or integrated into the aforementioned system for recognizing and segregating chicks by gender based on their wing pattern.

Figure 6:
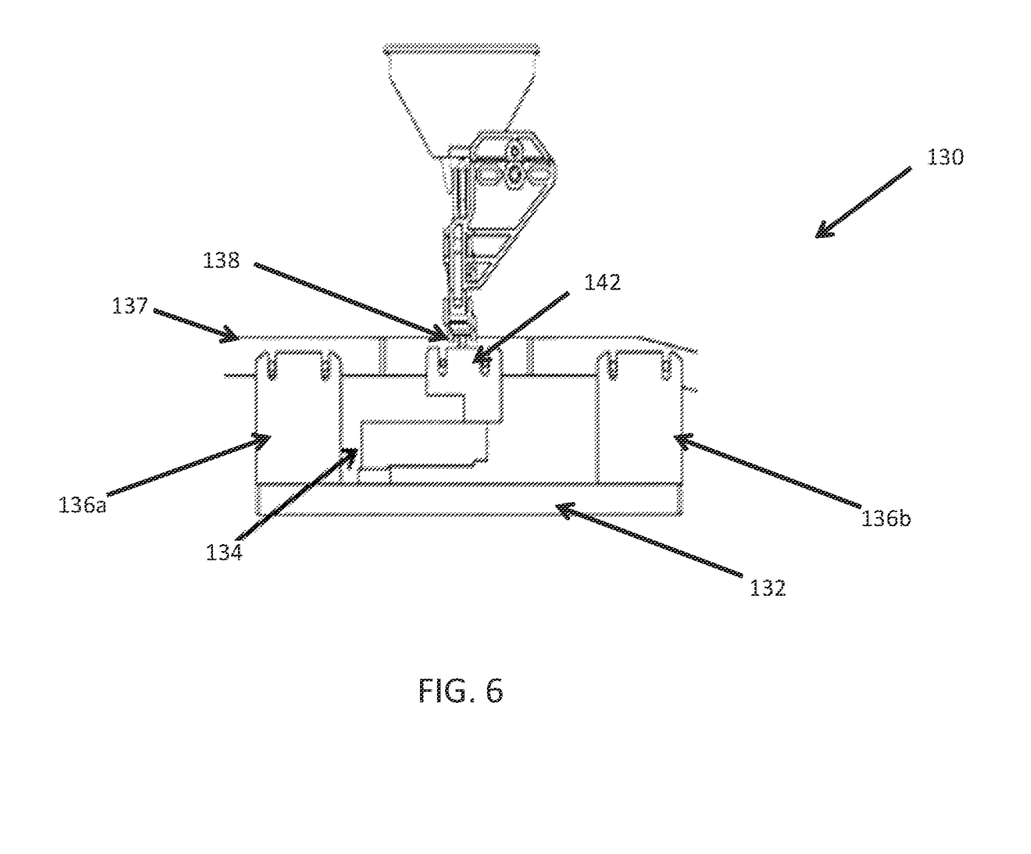
FIG. 6 is a perspective view of the weighing system according to an embodiment of the present invention.

FIG. 6 is a perspective view of the weighing system 130, which determines the health of a chick based on its weight (a healthy chick weight over 42-43 grams). The weighing system 130 includes, for example, a plane 132, a load cell 134 in communication with a processor (not shown), which is in further communication with a linked computer (not shown), and a first and second protrusions 136a and 136b extending upwards from the plane 132 so as to fasten the plane 132 to a surface 137. The load cell 134 is in communication, directly or indirectly, with the surface 137 so as to create a weighing position 138, in which weight readings are being produced. The weighing position 138 further includes an anchoring portion 142 configured to fasten the examined chick to the weighing position, while the weight readings are being produced.

The system 130 further includes, for example, two electromagnetic gates (not shown), a healthy chick gate, and a non-healthy chick gate located after the weighing position 138 and which are in communication with the linked computer.

In operation, as a chick enters the weighing system 130, it is directed to the weighing position 138 by, for example, being placed directly on the surface, which is, for example, a belt conveyor, or by being placed within, for example, a container similar in construction and operation to the containers of the system 100, disclosed above.

Once the chick reaches the weighing position 138, it is secured, either directly or through pin 116, to the weighing position 138 by anchoring portion 142. This action allows the load cell 134 to form, for example, over a hundred readings and transfer them to the processor. The processor identifies the "clean" readings (readings in which the chick did not move) and calculates the average value of the "clean" readings. This value is then transferred to the linked computer.

The linked computer compares the weight value transferred from the processor to a predetermined threshold, for example, a weight value of 42-43 grams, and sends a signal to either the healthy chick gate (if the weight value is equal or higher than the predetermined threshold) or the non-healthy chick gate (if the weight value is lower than the predetermined threshold) accordingly, causing the designated gate to open and receive the chick.

The system for detecting external body defects of chicks for assessing chicks' health includes, for example, a camera configured to obtain images of chicks, and a linked computer in communication with the camera configured to receive the images obtained by the camera and assess the health of the chicks via image processing. The chicks are directed to the camera's field of view by being placed, for example, directly on a conveyor, for example, a belt conveyor, or by being placed within, for example, a container similar in construction and operation to the containers of the system 100, disclosed above. The system further includes, for example, two electromagnetic gates, a healthy chick gate, and a non-healthy chick gate located after the camera's field of view and which are in communication with the linked computer.

In operation, as each chick enters the camera's field of view, the camera obtains images of the chick and transfers them to the linked computer. The linked computer processes the images and detects external body defects such as plume problems, a defective head, a rotated head, a crossed beak, and the like.

Once the image processing is finished and the chick exits the camera's field of view towards the gates, the linked computer sends a signal to either the healthy chick gate or the non-healthy chick gate, causing the designated gate to open and receive the chick.

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:

1. A system for recognizing and segregating chicks by gender according to their feathers pattern comprising:
   a separation unit including at least one first conveyor extending at least partially through said separation unit, said at least one first conveyor controlled by a computerized controller and configured to maintain a forward moving path of said plurality of chicks in a queue;
   a sorting unit configured to receive said plurality of chicks in a queue, said sorting unit includes:
   at least one second conveyor extending at least partially through said sorting unit configured to maintain a forward moving path; and,
   at least one container in communication with said at least one second conveyor such that said at least one container is moved vertically between a first position and a second position, while containing a chick of said plurality of chicks so as to cause the chick to spread its wings on its own volition in order to capture the fine distinction between the genders; and
   an optic unit including a camera configured to capture at least one image of said chick spreading its wings as said at least one container is moved vertically between said first position and said second position, said at least one image is then transferred to be image processed so as to determine the gender of said chick, wherein the image processing occurs in real-time and includes: separating pixels of the chick from a background, analyzing a contour of the chick to select images of the chick with wings outstretched, extracting features relating to the wings, and determining the gender of the chick according to these features; and
   a segregating unit controlled by said computerized controller and configured to physically segregate said plurality of chicks based on said determination of gender;
   wherein the at least one second conveyor keeps a forward movement of each container of the at least one container from the sorting unit towards the segregating unit in a horizontal movement, wherein each container has dimensions suited for the chick to refold its wings during the horizontal movement between sorting unit and segregating unit.

2. The system of claim 1, wherein said at least one container is configured to be moved upward or downward vertically between the first position and the second position by an upward vertical movement or a downward vertical movement of a moving element situated beneath the at least one container.

3. The system of claim 2, wherein the upward vertical movement of the moving element is concurrent with the vertically upward movement of the at least one container.

4. The system of claim 1, further comprising a turning aside mechanism designed to allow removal of the container content.

5. The system of claim 4, wherein said turning aside mechanism is controlled by the computerized controller.

6. The system of claim 1, additionally comprising a computerized controller configured for controlling said at least one second conveyor and said camera.

7. The system of claim 1, wherein said at least one second conveyor is one of: a belt conveyor, a U-shaped belt conveyor, a chain conveyor, a live roller conveyor, and a combination thereof.

8. The system of claim 1, wherein said at least one container has the shape of an inverted pyramid with a flattened vertex.

9. The system of claim 1, wherein said optic unit further includes a light source controlled by the computerized controller.

10. The system of claim 1, additionally comprising a wherein the segregating unit including at least one electromagnetic gate configured to receive said chick from said at least one container.

11. The system of claim 10, wherein said segregating unit is controlled by the computerized controller.

12. The system of claim 10 additionally comprising a counting mechanism configured to monitor the number of chicks passing through said at least one gate, said counting mechanism is controlled by the computerized controller.

13. The system of claim 12 additionally comprising a packaging machine configured to receive chicks from said at least one gate and pack them in a crates suitable for transporting chicks said packaging machine is controlled by the computerized controller.

14. The system of claim 1, wherein said one or more images are additionally used to detect body defects in said chick.

15. The system of claim 1, additionally comprising a weighing unit connected to said at least one conveyor of said sorting unit, said weighing unit includes a load cell configured to perform a plurality of weight readings of said at least one chick as said container reaches it so as to determine the health of said chick based on its weight.

16. The system of claim 15, further comprising electromagnetic gates that sort the chicks by weight.

17. The system of claim 15, wherein said load cell is in communication with a processor configured to calculate the actual weight of said chick.

18. The system of claim 2, wherein the moving element includes a pin portion and an intermediate portion.

19. The system of claim 2, wherein said upward vertical movement of said moving element is achieved though movement of a pin portion of said moving element along a slanting section of the sorting unit, wherein the movement of the pin portion includes an upward component.

20. The system of claim 19, wherein the movement of the pin portion along the slanting section slants upward as the forward moving path is traversed in a forward direction.

21. The system of claim 19, wherein an incline of the slanting section is not linear.

22. The system of claim 2, wherein the upward vertical movement of the moving element is concurrent with the upward vertical movement of said at least one container between said first position and said second position.

23. The system of claim 1, wherein the at least one container comprises a particular container and the particular container is configured to be moved upward vertically between the first position and the second position by an upward force sufficient to overcome gravity and accelerate the particular container upward.

24. The system of claim 1, wherein a slanting section is configured to allow the at least one container to move upward vertically between the first position and the second position while the at least one container moves forward along the forward moving path.

25. The system of claim 1, wherein the at least one container comprises a particular container and the particular container is configured to be moved upward vertically between the first position and the second position by an upward force sufficient to overcome gravity and accelerate the particular container upward.

* * * * *